(12) United States Patent
Kaufhold

(10) Patent No.: US 8,915,155 B1
(45) Date of Patent: Dec. 23, 2014

(54) METHOD AND DEVICE FOR MONITORING INTEGRITY OF WOODEN POSTS

(71) Applicant: United Technologists Europe Limited, Suffolk (GB)

(72) Inventor: Frank Gerwin Kaufhold, Suffolk (GB)

(73) Assignees: United Technologists Europe Limited, Suffolk (GB); Frank Gerwin Kaufhold, Suffolk (GB)

( * ) Notice: Subject to any disclaimer, the term of this patent is extended or adjusted under 35 U.S.C. 154(b) by 0 days.

(21) Appl. No.: 14/122,990

(22) PCT Filed: Jan. 15, 2013

(86) PCT No.: PCT/GB2013/050076
§ 371 (c)(1),
(2), (4) Date: Nov. 27, 2013

(87) PCT Pub. No.: WO2013/121170
PCT Pub. Date: Aug. 22, 2013

(30) Foreign Application Priority Data

Feb. 17, 2012 (GB) .................................. 1202760.3

(51) Int. Cl.
*G01N 19/00* (2006.01)
*G01N 33/46* (2006.01)
(52) U.S. Cl.
CPC ................ *G01N 33/46* (2013.01); *G01N 19/00* (2013.01)

USPC ........................................................ 73/865.8
(58) Field of Classification Search
CPC .............................. G01N 19/00; G01N 33/46
USPC ...................................... 73/78, 82, 85, 865.8
See application file for complete search history.

(56) References Cited

U.S. PATENT DOCUMENTS 4,329,882 A    5/1982   Kaup

FOREIGN PATENT DOCUMENTS

| AU | 594447 B2 | 3/1990 |
| DE | 10031395 A1 | 4/2001 |
| GB | 2242029 A | 9/1991 |
| GB | 2301191 A | 11/1996 |
| JP | 7244044 A | 9/1995 |
| WO | 01/65253 A2 | 9/2001 |

*Primary Examiner* — Hezron E Williams
*Assistant Examiner* — David Z Huang
(74) *Attorney, Agent, or Firm* — McGarry Bair PC

(57) ABSTRACT

A device (10) for monitoring the integrity of a wooden post (40) including an outer sleeve (11), a moveable pin (12), a spring (24) and a measuring rod (50). The outer sleeve (11) is adapted to be mounted in a pre-formed recess (41) of complementary size and shape extending from the outer surface (43) of a wooden post (40) substantially into the center (45) thereof. The moveable pin (12) is mounted within the outer sleeve (11) and has a head (18) arranged normally to bear against wood at the center (45) of the post (40). The spring (24) is arranged to urge the pin head (18) against wood at the center (45) of the post (40). The measuring rod (50) denotes any movement of the pin (12) further into the post (40).

20 Claims, 3 Drawing Sheets

METHOD AND DEVICE FOR MONITORING INTEGRITY OF WOODEN POSTS

CROSS-REFERENCE TO RELATED APPLICATIONS

This application is a National Phase application of International Application No. PCT/GB2013/050076, filed Jan. 15, 2013, which claims the benefits of GB1202760.3, filed Feb. 17, 2012, all of which are incorporated herein by reference in their entireties.

This invention relates to a method and device for monitoring the integrity of a wooden post, such as a telegraph pole. In particular, the invention relates to such a method and device for ascertaining whether the structural integrity of telegraph poles may have been compromised by rot. The terms "pole" and "post" are used interchangeably herein.

Wooden telegraph poles (sometimes referred to as utility poles) are used to carry overhead telephone cables and power lines. Periodic access to the overhead cables is required for routine maintenance and repair, and this is generally achieved by a technician climbing the pole. In order for this to be done safely, the technician must first ascertain that the pole has sufficient integrity to support his weight.

Being constructed of wood and partially buried in the ground, all telegraph poles will eventually succumb to rot, which compromises the structural integrity of the pole and makes it unsafe for a technician to climb. Telegraph poles are generally pressure-treated with wood preservative such as creosote to prevent rot and so extend the lifetime of the pole—but despite the pressure treatment, the preservative will never fully penetrate into the centre of the pole. As a consequence, the pole will eventually rot in the centre, with the outer layers of wood often remaining more or less intact, effectively forming a hollow tubular structure. A pole in this state may still perform adequately in its primary function of supporting overhead cables, and may exhibit no external signs of degradation. However, a hollow pole is likely to be incapable of safely supporting the weight of a technician.

The useful lifetime of a wooden telegraph pole will vary according to the climatic conditions of the area in which the pole is installed—for example a pole in a particularly wet or humid area will rot faster, and so need replacing sooner, than a pole in an area with a dry climate. In temperate climates such as that of the United Kingdom, the typical lifetime of telegraph pole is around 20 years. Network operators generally seek to replace the oldest poles in their network on a rolling basis, but this can be a difficult operation to monitor due to the sheer number of poles in a network. Moreover, it is essentially impossible to predict exactly when any particular pole will have reached the acceptable limits of structural integrity from the point of view of technician safety.

Existing proposals for the solution of the above identified problems are considered to be unsatisfactory on the basis of safety, reliability, efficiency and cost. One existing method for verifying the structural integrity of a pole prior involves the measurement of the acoustic properties of a pole, and comparison of the results with known measurements of structurally sound poles. Problems with this method include the cost of the acoustic measurement equipment, the level of skill required for the equipment to be operated—which may necessitate an additional technician, and issues surrounding the reliability of the results, since these are based on an indirect measurement—i.e. measurement of a property of the wood (acoustics) affected by rot, but not direct measurement of the extent of the rot itself.

A crude, but widely used, variant of this method involves the technician simply tapping the pole with a hammer, and making an assessment of the pole's structural integrity simply on the basis of the sound made. Clearly, this method is highly subjective since it relies on the experience and judgment of the individual technician, and cannot be considered safe even for the most experienced technician.

The present invention seeks to address the above-identified problems by proposing a reliable and economic device and method for safely and efficiently monitoring the integrity of wooden posts, such as telegraph poles, which device and method provide an instant indication based on a direct measurement of the extent of rot within the centre of the pole.

According to a first aspect of the present invention there is provided a device for monitoring the integrity of a wooden post, comprising:

an outer sleeve adapted to be mounted in a pre-formed recess of complementary size and shape extending from the outer surface of a wooden post substantially into the centre thereof;

a moveable pin mounted within the outer sleeve and having a head arranged normally to bear against wood at the centre of said post;

driving means for urging the pin head against wood at the centre of said post; and indicating means for denoting any movement of the pin further into said post.

The present invention has been developed for use in monitoring the structural integrity of telegraph poles, and in particular for monitoring the extent to which the pole may have rotted at its centre, and the invention is therefore described herein with particular reference to this use. However, it should be understood that the scope of the present invention encompasses its use for monitoring the integrity of substantially all types of wooden posts.

The terms "normal" and "normally" as used herein with reference to the position of the pin and pin head, refer to the condition of the device of the present invention when installed in a new wooden post, before any rotting of the post has occurred.

The device according to the present invention operates on the principle that the hard wood present at the centre of a new post will resist the movement of the pin head further into the post, despite the driving means urging the pin head against the wood. As the wood at the centre of the post rots and becomes soft, the driving means will urge the pin further into the post, which movement will be denoted by the indicating means, thus enabling a technician to ascertain the integrity of the post by periodically monitoring the indicating means.

The sleeve and pin are preferably each generally cylindrical, and of substantially equal length. The pin head preferably has a conical profile at the end thereof adapted to bear against wood at the centre of said post. The sleeve is preferably adapted to be permanently installed in the wooden post.

In order to facilitate the operation of the device, the sleeve preferably has a first aperture at a first end thereof, adapted to be located at or adjacent the outer surface of the wooden post, and a second aperture at a second end therefore, adapted to be located at or adjacent the centre of said wooden post. The pin preferably has a first end arranged normally to be located within the first aperture of the sleeve, and a second end having the pin head, arranged normally to be located within the second aperture of the sleeve.

The location of the first end of the pin within the first aperture of the sleeve is normally visible from the outer surface of the wooden post, such that the first aperture of the sleeve and the first end of the pin together constitute said indicating means for denoting any movement of the pin further into said post. That is to say if, on periodic monitoring of the indicating means, the first end of the pin is visible in, and substantially flush with, the first aperture of the sleeve, then it is apparent that the pin head has not moved further into the post from its normal position, and thus that no rotting of the post has occurred. However if, on periodic monitoring of the indicating means, the first end of the pin is not visible in the first aperture of the sleeve, or is displaced inwardly relative to said first aperture, then it is apparent that the pin has moved further into the post, consequent upon the presence of rot in the centre of the post. The degree of rot in the centre of the post will be denoted by the degree to which the first end of the pin is displaced inwardly relative to the first aperture of the sleeve.

In a preferred embodiment of the present invention, the indicating means preferably further comprises a measuring rod adapted for insertion into the first aperture of the sleeve, so as to determine the extent of movement of the pin into said post. The measuring rod constitutes a separate component, not permanently installed in the post, which will be utilised by the technician for periodic monitoring of the position of the pin. The measuring rod may be provided with markings so as visually to indicate the extent of movement of the pin into said post, when the measuring rod is inserted into the first aperture of the sleeve. The measuring rod is preferably calibrated to indicate a pre-determined acceptable limit of movement of the pin, corresponding to a pre-determined acceptable limit of the extent of rot within the post beyond which the structural integrity of the post is considered unsafe for a technician to climb.

In order to facilitate the secure mounting of the sleeve in the recess, the sleeve preferably comprises an external screw thread extending partially down the length thereof adjacent the first end. The sleeve preferably further comprises a hexagonal bolt head fitting at the first end thereof, around the first aperture.

The driving means for urging the pin head against the wood at the centre of the post preferably comprises a spring, and most preferably a high tensile spring. The tensile strength of the spring can be selected in order to calibrate the device, depending on the type of wood and size of pole.

The driving means preferably further comprise a first shoulder provided on the sleeve, part-way along the internal surface thereof, and a second shoulder formed on the pin head at is the junction with the pin, wherein the spring is normally arranged to be compressed between said first and second shoulders. The spring is normally held in a state of compression by the hard wood at the centre of the post resisting the further motion of the pin head. As the wood rots, the compression in the spring is released, thus urging the pin head further into the wood. The device preferably comprises a removable safety clip to retain the pin in its normal position within the sleeve during installation.

In order to provide a seal against the ingress of moisture, the pin is preferably provided with one or more O-rings. Most preferably, the pin is provided with one O-ring adjacent its junction with the pin head, and one O-ring adjacent its first end. The device may desirably also be sealed with silicone sealant around the boundary between the sleeve and the wooden post. A removable protective cap may also be provided to cover the first aperture of the sleeve. The device is preferably formed of metal, most preferably steel.

The scope of the present invention extends to include a method of monitoring the integrity of a wooden post, such as a telegraph pole, utilising a device according to the first aspect of the present invention as hereinbefore described.

Therefore, according to a second aspect of the present invention, there is provided a method of monitoring the integrity of a wooden post comprising the steps of:
forming a recess, extending from the outer surface of said wooden post substantially to the centre thereof;
locating in said recess a device according to the first aspect of the present invention as hereinbefore described; and
periodically monitoring any movement of the device pin further into the post.

The recess is preferably formed by drilling, so as to be of complementary size and shape to the device. Most preferably, the recess and device are each generally cylindrical.

The recess is preferably formed at an angle in the range of from 30° to 60°, most preferably 45° relative to the horizontal, and arranged such that the centre thereof is at or below ground level, but with the end of said recess located on the surface of the wooden post remaining above ground level when the post is installed.

The method according to the second aspect of the present invention preferably comprises an additional step of periodically monitoring movement of the device pin further into the post utilising a measuring rod as hereinbefore described. The method may also further comprise an additional preliminary step of calibrating the measuring rod to indicate a pre-determined acceptable limit of movement of said device pin, corresponding to a pre-determined acceptable limit of the extent of rot within the post beyond which the structural integrity of the post is considered unsafe for a technician to climb.

The step of locating the device in the recess in the wooden post preferably involves permanently installing the sleeve, most preferably by means of the external screw-thread thereon as hereinbefore described. The step of locating the device in the recess preferably also involves sub-steps of: lubricating the sleeve and/or the recess to facilitate the insertion of the sleeve into the recess; and/or sealing the sleeve in the recess so as to prevent ingress of moisture. Silicone sealant may be utilised for the sealing step, and may also be utilised for the lubrication step.

During location of the device in the recess, the device pin is preferably held in its normal position by means of a safety clip. The step of locating the device in the recess is then preferably followed by a sub-step of removing said safety clip to prime the device.

In order that the present invention may be clearly understood, a preferred embodiment thereof will now be described in detail, though only by way of example, with reference to the accompanying drawings, in which.

Figure 1:
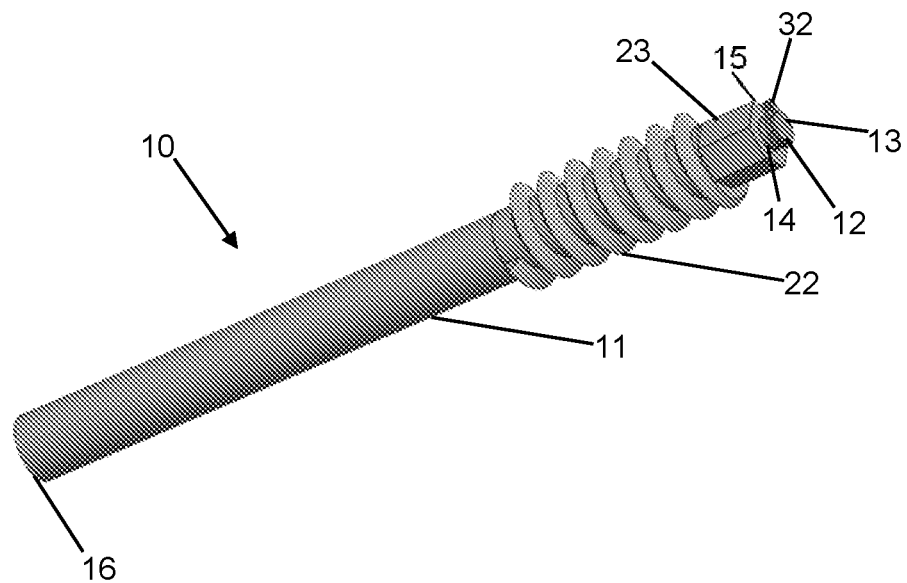
FIG. 1 shows a perspective view of a device for monitoring the integrity of a wooden post, according to the first aspect of the present invention.
Figure 2:
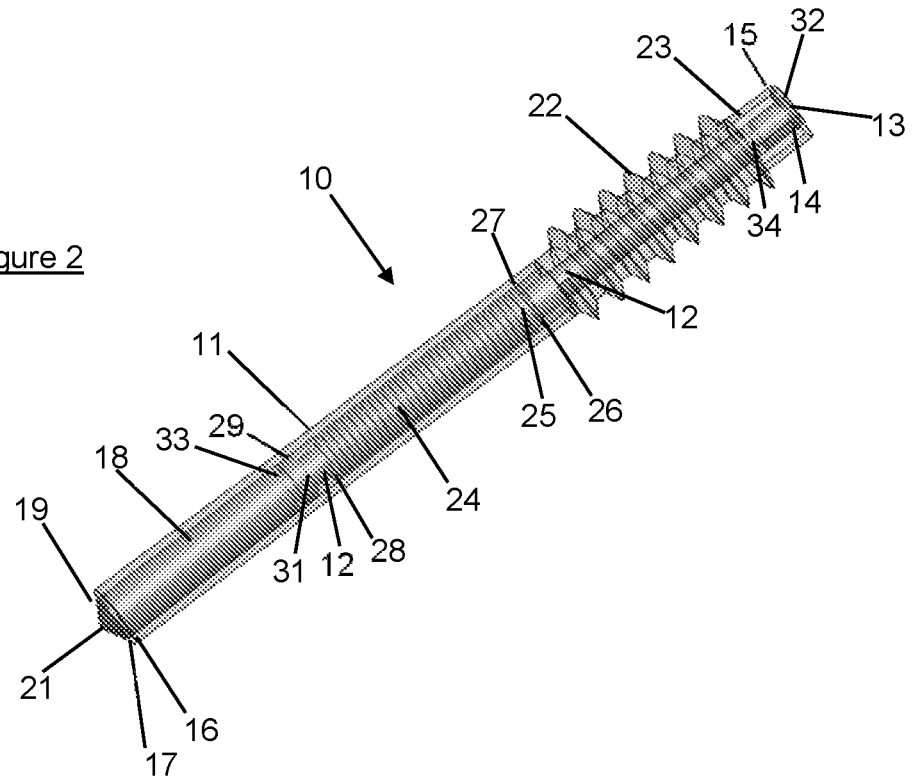
FIG. 2 shows a partially cross-sectional view of the device of FIG. 1.
Figure 3:
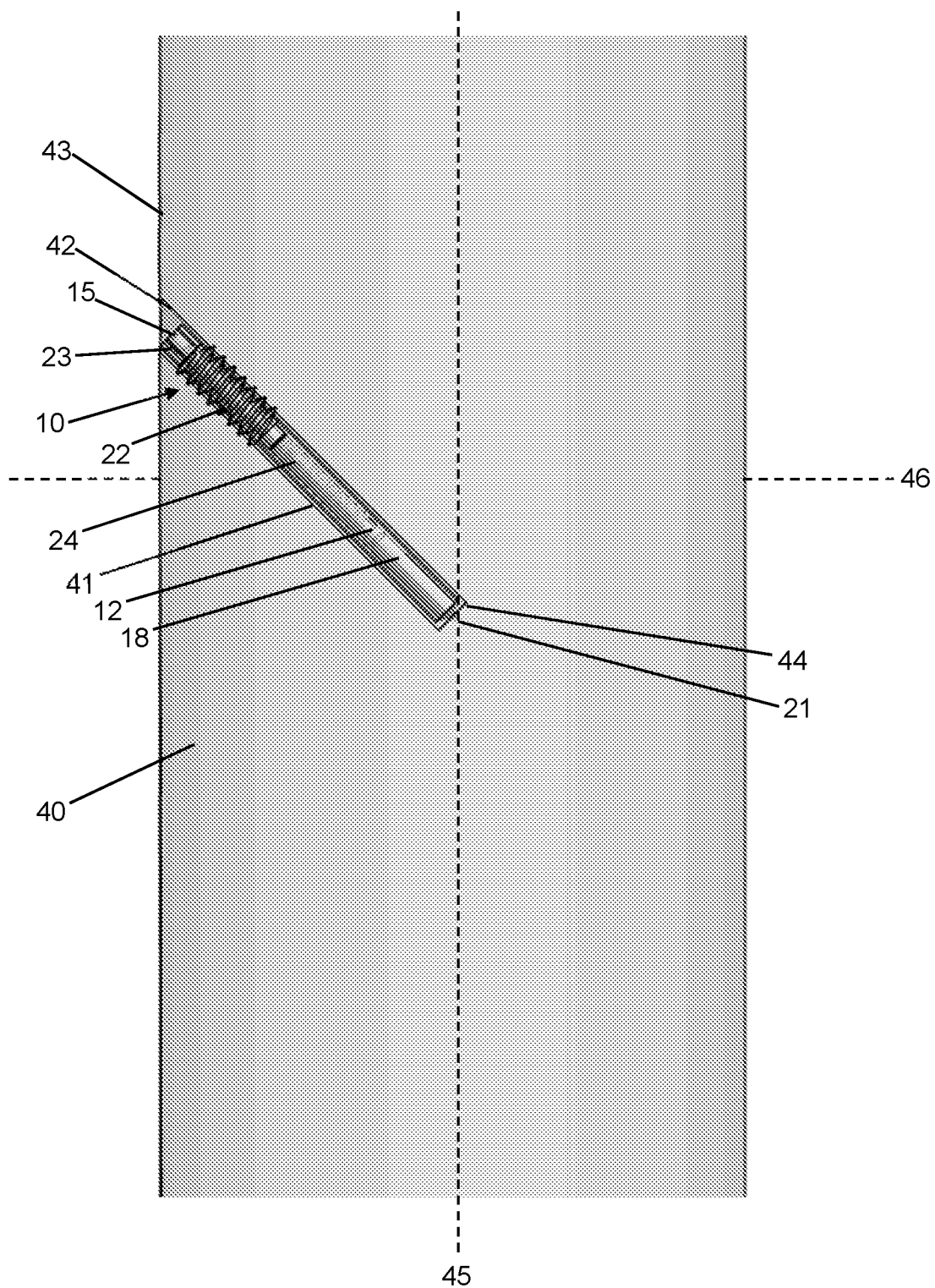
Figure 4:
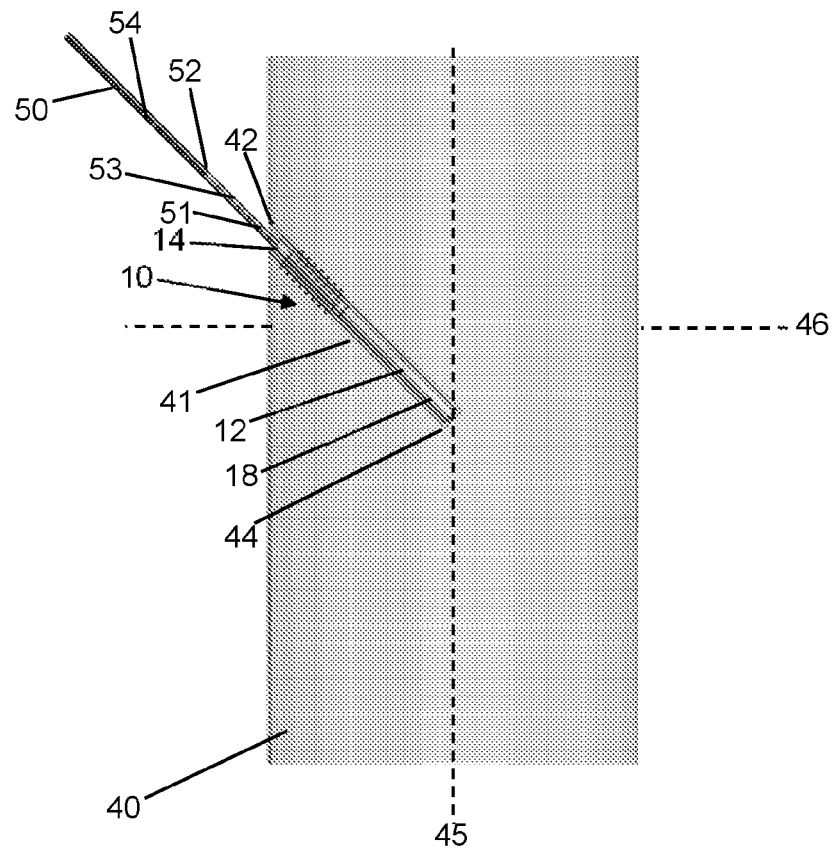
Figure 5:
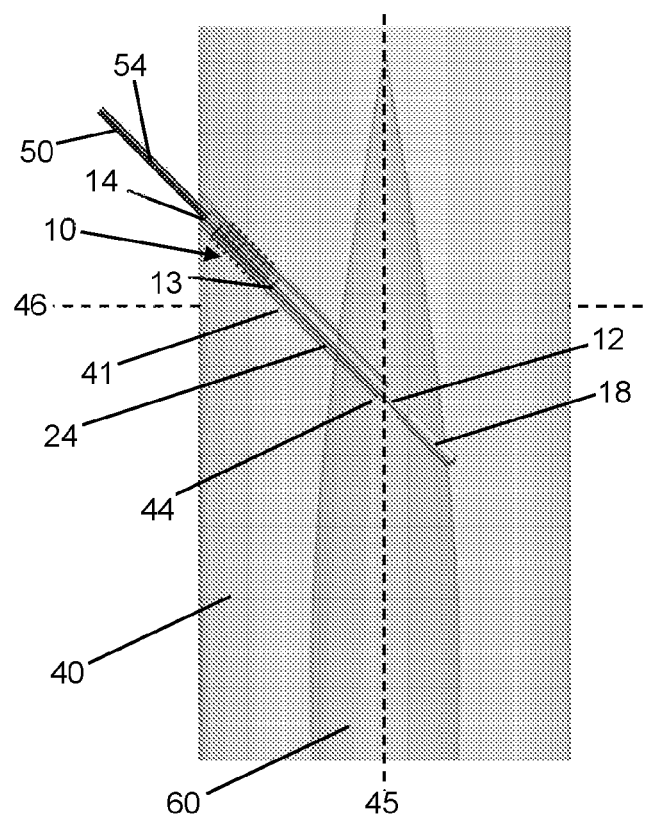

FIG. 3 shows a cross-sectional view of the device of FIGS. 1 and 2 installed in a new wooden post so as to be utilised in a method according to the second aspect of the present invention; and FIG. 4 shows a cross-sectional view of the device and post of FIG. 3 during monitoring when the wooden post is new; and FIG. 5 shows a cross-sectional view the device and post of FIGS. 3 and 4 during monitoring when the wooden post has rotted internally.

Referring first to FIGS. 1 and 2, there is shown a preferred embodiment of a device, generally indicated 10, according to a first aspect of the present invention, for monitoring the integrity of a wooden post. The device 10 comprises an outer sleeve 11 having a moveable pin 12 mounted therein, as can best be seen from FIG. 2. The sleeve 11 is shown in FIG. 2 in a cross-sectional view in order to show the pin 12 therewithin. As can be seen, the pin 12 is substantially wholly enclosed within the sleeve 11, and hence only a first end 13 of the pin 12 can be seen in FIG. 1, said first end 13 protruding through a first aperture 14 at the first end 15 of the sleeve 11. As can also best be seen from FIG. 2, the second end 16 of the sleeve 11 has a second, larger aperture 17, within which is located a pin head 18 carried on the second end 19 of the pin 12. The pin head 18 terminates in a generally conical end 21.

As can best be seen from FIG. 1, the sleeve 11 is provided with an external screw thread 22 adjacent its first end 15, to enable the device 10 to be securely mounted within a recess in a wooden post. The first end 15 of the sleeve 11 is also provided with a hexagonal bolt head fitting 23, around the first aperture 14, to enable the use of conventional tools for mounting the device 10 in a post.

Referring again to FIG. 2, it can be seen that the pin 12 passes through the centre of a spring 24. The spring 24 is arranged to bear at one end 25 thereof against a first-shoulder 26 formed part-way down the internal surface 27 of the sleeve 11, and at its other end 28 against a second shoulder 29 formed at the junction 31 of the pin 12 and the pin head 18. As will be described in more detail below with reference to FIGS. 3 to 5, when the device 10 is installed in a new wooden post, the pin 12 is required to be in its "normal" position—i.e. fully retracted into the sleeve 11, with the first end 13 of the pin 12 located in the first aperture 14 of the sleeve 11. This requires the spring 24 to be fully compressed between the first and second shoulders 26, 29, and held in that compressed state, else the pin 12 would be fired out of the second end 16 of the sleeve 11, with some force. In order to achieve this, the first end 13 of the pin 12 is provided with a safety clip 32, as can best be seen in FIG. 1. The safety clip 32 retains the pin 12 in position during installation of the device 10, and is then removed to prime the device 10 ready for use.

In order to provide a seal against the ingress of moisture, the pin 12 is provided one rubber O-ring in a first groove 33 adjacent the junction 31 of the pin 12 with the pin head 18, and one rubber O-ring in a second groove 34 adjacent the first end 13 of the pin 12. Note that for clarity, the rubber O-rings themselves are omitted from FIG. 2, though the grooves 33, 34 for receiving them are clearly visible.

A preferred embodiment of a method, according to the second aspect of the present invention, of monitoring the integrity of a wooden post, utilising a device 10 according to the first aspect of the present invention, will now be described with reference to FIGS. 3 to 5.

Referring first to FIG. 3, a new wooden post 40 to be used as a telegraph pole has a cylindrical recess 41 drilled therein. The cylindrical recess 41 is sized so as to be complementary to the device 10 according to the first aspect of the present invention, to ensure a secure fit, and so as to extend from an upper 42 end at the outer surface 43 of the wooden post 40 to a lower end 44 substantially at the centre 45 of the post 40. The recess 41 is angled at approximately 45° relative to the horizontal, such that the top end 42 remains above ground level 46 whilst the lower end 43 is located below ground level 46, when the post 40 is installed.

The device 10 is then inserted into the recess 41 using a conventional power drill and driver, or similar, engaged with the hexagonal bolt head fitting 23. A silicone-based lubricant is used to ease the insertion of the device 10 into the recess 41, and subsequently to act as a sealant against the ingress of moisture. As the device 10 is driven into the recess 41, the external screw thread 22 engages with the wooden post 40 to ensure a secure fit. The device 10 is correctly located in the recess 41 when the end 21 of the pin head 18 bears against the hard wood at the centre 45 of the post 40 (i.e. at the lower end 44 of the recess 41). The first end 15 of the device 10, carrying the aperture 14 will now be either flush with the surface 43 of the post 40, or if desired may be slightly counter-sunk below the surface 43, as shown in FIG. 3.

During installation, it is necessary for the pin 12 to be held in its "normal" position, with the spring 24 held in a state of compression between the first and second shoulders 26, 29, using the safety clip 32, as described above with reference to FIGS. 1 and 2. Once the device 10 is installed in the post 40 as shown in FIG. 2, the safety clip 32 can then be removed in order to prime the device 10 ready for use. The motion of the pin head 18 is then resisted by the hard wood at the centre 45 of the post 40, against the force of the spring 24, which would otherwise drive the pin 12 further into the post 40.

Referring now to FIG. 4, this shows the device 10 shortly after installation in the post 40, and before any rotting of the post 40 has taken place. The pin head 18 thus still bears against the hard wood at the centre 45 of the post 40 (that is, at the lower end 44 of the recess 41), and no movement of the pin 12 has taken place. Although not visible from FIG. 4, the first end 13 of the pin 12 will thus still be substantially flush with the aperture 14 at the first end 15 of the device 10. Depending on the degree to which the first end 15 of the device is counter-sunk into the upper end 42 of the recess 41, it may be possible for a technician to verify this from a visual inspection of the upper end 42 of the recess 41. However, for a more reliable indication, and to obtain an accurate measurement of any movement of the pin 12 into the post 40, the technician uses a measuring rod 50 for periodic monitoring of the post 40.

The measuring rod 50 is in the nature of a dip-stick, and is inserted into the aperture 14 at the first end of the device 10, until contact is made between the measuring rod 50 and the first end 13 of the pin 12. The measuring rod 50 carries graduated markings 51, to be read at the point where the rod 50 enters the aperture 14, to indicate the extent of any movement of the pin 12.

The measuring rod 50 is also calibrated to indicate a pre-determined acceptable limit 52 of movement of the pin 12, corresponding to a pre-determined acceptable limit of the extent of rot within the post 40 beyond which the structural integrity of the post 40 is considered unsafe for a technician to climb. As can be seen from FIG. 4, for ease of reference for the technician, the measuring rod 50 is divided into colour-coded zones either side of the limit 52, with a green coloured "safe" zone 53 formed on the lower part of the rod 50, and a red coloured "danger" zone 54 formed on the upper part of the rod 50. As with the graduated markings 51, the reading of the "safe" and "danger" zones 53, 54 is to be carried out at the point where the rod 50 enters the aperture 14. As can be seen from FIG. 4, since there has been no movement of the pin 12, the measuring rod 50 returns a reading in the "safe" zone 53, and so the post 40 is safe to climb.

Referring now to FIG. 5, this shows the same post 40, with the device 10 still permanently installed therein, some years later when significant rotting of the post 40 has occurred. Rotting of treated wooden posts 40 occurs from the bottom upwards and from the centre 45 outwards, in a rising, generally conical pattern 60, as shown in FIG. 5. The wood in the rotten area 60 of the post 40 will be significantly softer than in the remainder of the post 40. As such, once the rot 60 reaches the lower end 44 of the recess 41, the wood at the centre 45 of the post 40 is no longer capable of resisting the movement of the pin head 18 and the expansion of the spring 24. The spring 24 thus expands, driving the pin head 18 out through the lower end 44 of the recess 41, and through the rotten area 60 until it again reaches hard wood in the remainder of the post 40.

Periodic monitoring of the post 40 by inserting the measuring rod 50 into the aperture 14, now requires the rod 50 to be inserted considerable further into the device 10 before contact is made between the rod 50 and the first end 13 of the pin 12. Consequently, the measuring rod 50 now returns a reading in the "danger" zone 54, indicating that the post 40 is unsafe for the technician to climb, and is in need of replacement.

The invention claimed is:

1. A device for monitoring the integrity of a wooden post, comprising:
    an outer sleeve adapted to be mounted in a pre-formed recess of complementary size and shape extending from the outer surface of a wooden post substantially into the centre thereof;
    a moveable pin mounted within the outer sleeve and having a head arranged normally to bear against wood at the centre of said post;
    driving means comprising a spring for urging the pin head against wood at the centre of said post; and
    indicating means for denoting any movement of the pin further into said post.

2. A device as claimed in claim 1, wherein the sleeve and pin are each substantially cylindrical.

3. A device as claimed in claim 1, wherein the outer sleeve and the pin are of substantially equal length.

4. A device as claimed in claim 1, wherein the sleeve is adapted to be permanently installed in said wooden post.

5. A device as claimed in claim 1, wherein the outer sleeve has a first aperture at a first end thereof, adapted to be located at or adjacent the outer surface of said wooden post, and a second aperture at a second end thereof, adapted to be located at or adjacent the centre of said wooden post.

6. A device as claimed in claim 5, wherein the pin has a first end arranged to be located within the first aperture of the sleeve, and a second end having the pin head, arranged to be located with the second aperture of the sleeve.

7. A device as claimed in claim 6, wherein the location of the first end of the pin within the first aperture of the sleeve is visible, such that said first aperture and said first end of the pin constitute said indicating means for denoting any movement of the pin further into said post.

8. A device as claimed in claim 7, wherein said indicating means for denoting movement of the pin into the post further comprise a measuring rod adapted for insertion into the first aperture of the sleeve, so as to determine the extent of movement of the pin into said post.

9. A device as claimed in claim 8, wherein the measuring rod is provided with markings so as visually to indicate the extent of movement of the pin into said post.

10. A device as claimed in claim 8, wherein the measuring rod is calibrated to indicate a pre-determined acceptable limit of movement of the pin.

11. A device as claimed in claim 1, wherein the sleeve comprises an external screw thread extending partially down the length thereof adjacent a first end thereof, to enable the sleeve to be securely mounted within said recess.

12. A device as claimed in claim 1, wherein the outer sleeve comprises a hexagonal bolt head fitting at a first end thereof, to facilitate mounting within said recess.

13. A device as claimed in claim 1, wherein the spring is a high tensile spring.

14. A device as claimed in claim 1, further comprising a first shoulder provided on the sleeve, part-way along the internal surface thereof, and a second shoulder formed at the junction of the pin with the pin head, and wherein the spring is normally arranged to be compressed between said first and second shoulders.

15. A device as claimed in claim 1, wherein the pin is provided with one or more O-rings to provide a seal against the ingress of moisture.

16. A device as claimed in claim 15, wherein the pin head is provided with an O-ring adjacent its junction with the pin.

17. A device as claimed in claim 15, wherein the pin is provided with an O-ring adjacent its first end.

18. A device as claimed in claim 1, wherein the pin head has a conical profile at the end thereof adapted to bear against wood at the centre of said post.

19. A device as claimed in claim 1, further comprising a safety clip to retain the pin within the sleeve during installation.

20. A method of monitoring the integrity of a wooden post comprising the steps of:
    forming a recess, extending from the outer surface of said wooden post substantially to the centre thereof;
    locating in said recess a device, the device comprising:
    an outer sleeve adapted to be mounted in the recess, the recess being of complementary size and shape;
    a moveable pin mounted within the outer sleeve and having a head arranged normally to bear against wood at the centre of said post;
    driving means comprising a spring for urging the pin head against wood at the centre of said post; and
    indicating means for denoting any movement of the pin further into said post; and
    periodically monitoring any movement of the device pin further into the post.

* * * * *